United States Patent [19]
Mermoud et al.

[11] Patent Number: 5,324,478
[45] Date of Patent: Jun. 28, 1994

[54] GAS GENERATING APPARATUS

[75] Inventors: Francois Mermoud, Westmont; Michael D. Brandt, Chicago, both of Ill.

[73] Assignee: American Air Liquide, New York, N.Y.

[21] Appl. No.: 931,656

[22] Filed: Aug. 17, 1992

Related U.S. Application Data

[63] Continuation of Ser. No. 788,174, Nov. 5, 1991, abandoned, which is a continuation of Ser. No. 310,746, Feb. 14, 1989, abandoned, which is a continuation-in-part of Ser. No. 85,888, Aug. 14, 1987, Pat. No. 4,849,174.

[51] Int. Cl.$^5$ .............................................. G01N 33/00
[52] U.S. Cl. .............................. 422/62; 422/83; 422/112; 422/116; 422/187; 137/88; 239/34
[58] Field of Search ................. 422/62, 83, 112, 116, 422/187, 189; 239/34, 432, 7, 8, 3; 137/88

[56] References Cited

U.S. PATENT DOCUMENTS 4,023,587  5/1977  Dobritz ........................ 137/88
4,399,942  8/1983  Chand ......................... 422/101

Primary Examiner—Lyle A. Alexander
Attorney, Agent, or Firm—Curtis, Morris & Safford

[57] ABSTRACT

Gas generating apparatus in which a supply of carrier gas is mixed with an impurity gas that permeates through the membrane of an impurity gas generator. A dopant gas is supplied to the impurity gas generator through a pressure controller which operates in response to a pressure monitor that monitors the pressure of the dopant gas supplied to the impurity gas generator. As the monitored pressure of the supplied dopant gas changes, the pressure of that supplied gas likewise changes in a manner which maintains a substantially constant flow rate of the impurity gas through the membrane to be mixed with a carrier gas.

9 Claims, 2 Drawing Sheets

GAS GENERATING APPARATUS

CROSS REFERENCE TO RELATED APPLICATION

This application is a continuation of application Ser. No. 07/788,174, filed Nov. 5, 1991 now abandoned which is a continuation of application Ser. No. 07/310.746, filed Feb. 14, 1989, now abandoned, which is a continuation-in-part of copending U.S. Application Ser. No. 085,888 filed Aug. 14, 1987, now U.S. Pat. No. 4,849,174.

BACKGROUND OF THE INVENTION

This invention relates to gas generating apparatus and more particularly to such apparatus for calibrating analyzers or similar equipment.

There has been developed a device for emitting a gas at a more or less constant rate into a moving fluid medium to produce a known concentration of the gas in the fluid medium and hence facilitate the calibration of certain types of analytical equipment. The gas is enclosed in a cylinder under pressure, in equilibrium with its liquid phase or solely in its gaseous phase, and the gas permeates through a permeate material to fill an accurately dimensioned passage through one end of the cylinder. In some cases the cylinder is divided into two chambers, one for holding the gas in liquified form and the other for holding it in gaseous form, such that it permeates through a membrane between the two chambers and then through another membrane positioned at the exit from the second chamber. Representative devices of this type are disclosed, for example, in U.S. Pat. Nos. 3,856,204 and 4,399,942.

Heretofore, difficulties have been encountered with apparatus of the foregoing type, and these difficulties were of special moment with respect to the need to maintain an extremely constant rate of emission of the gas from the cylinder into the fluid medium. As described in the foregoing U.S. Patents, attempts to resolve these difficulties for the most part were directed toward maintaining a constant temperature around the cylinder. These attempts were not entirely satisfactory, however, and the use of such prior apparatus to calibrate many types of analyzers continued to provide inaccurate and nonreproducable results.

It is of course well known that there is a need in the semi-conductor industry, for example, to accurately measure the concentration of impurities, such as water vapor, in the gases used during the manufacture of integrated circuits. In particular, there is a need to calibrate analyzers, such as hygrometers, accurately in the 0.001 to 1.0 ppm range, and this need has not been fulfilled by the prior gas generating apparatus of the type referred to above.

Summary

One general object of this invention, therefore, is to provide new and improved gas generating apparatus which is particularly well suited for the calibration of analytical equipment, particularly in the 0.001 to 1.0 ppm range.

More specifically, it is an object of the invention to provide such gas generating apparatus in which the concentration of the impurity or dopant gas introduced into the fluid medium remains constant over a wide range.

Another object of the invention is to provide gas generating apparatus which is economical to manufacture and thoroughly reliable in operation.

In an illustrative embodiment of the invention, the apparatus includes a fluid medium in the form of a supply of vector or carrier gas which contains gaseous impurities. A mass flow controller is utilized to meter the carrier gas from the supply and to discharge the gas at a precise massic flow rate. The gaseous impurities are removed from the carrier gas, and an impurity generator is employed to inject a constant flow of dopant or impurity gas through a membrane into the carrier gas stream to provide a gaseous mixture containing a precise amount of the injected impurity gas. The mixture is then supplied to a gas analyzer to be calibrated.

In accordance with one feature of certain advantageous embodiments of the invention, the impurity gas is continuously supplied to the gas generator to maintain a constant pressure on the side of the membrane remote from that facing the carrier gas. The arrangement is such that the exponential decay of the permeation rate through the membrane that would otherwise occur is substantially reduced, and the permeation rate is kept relatively constant throughout the membrane's useful life. Accordingly, the impurity level generated in the carrier gas at a given temperature is only a function of the flow of carrier gas past the membrane, and this carrier gas flow is regulated and kept constant by the mass flow controller.

In accordance with another feature of the invention, in several important embodiments, the pressure of the carrier gas into which the impurity gas is injected is carefully monitored in order to maintain a constant but adjustable pressure on the side of the membrane exposed to the carrier gas. With this arrangement, fluctuations in the permeation rate of the impurity gas through the membrane are substantially reduced.

The present invention, as well as further objects and features, thereof, will become more fully apparent from the following detailed description of certain preferred embodiments, when read with reference to the accompanying drawings.

DESCRIPTION OF CERTAIN PREFERRED EMBODIMENTS

Figure 1:
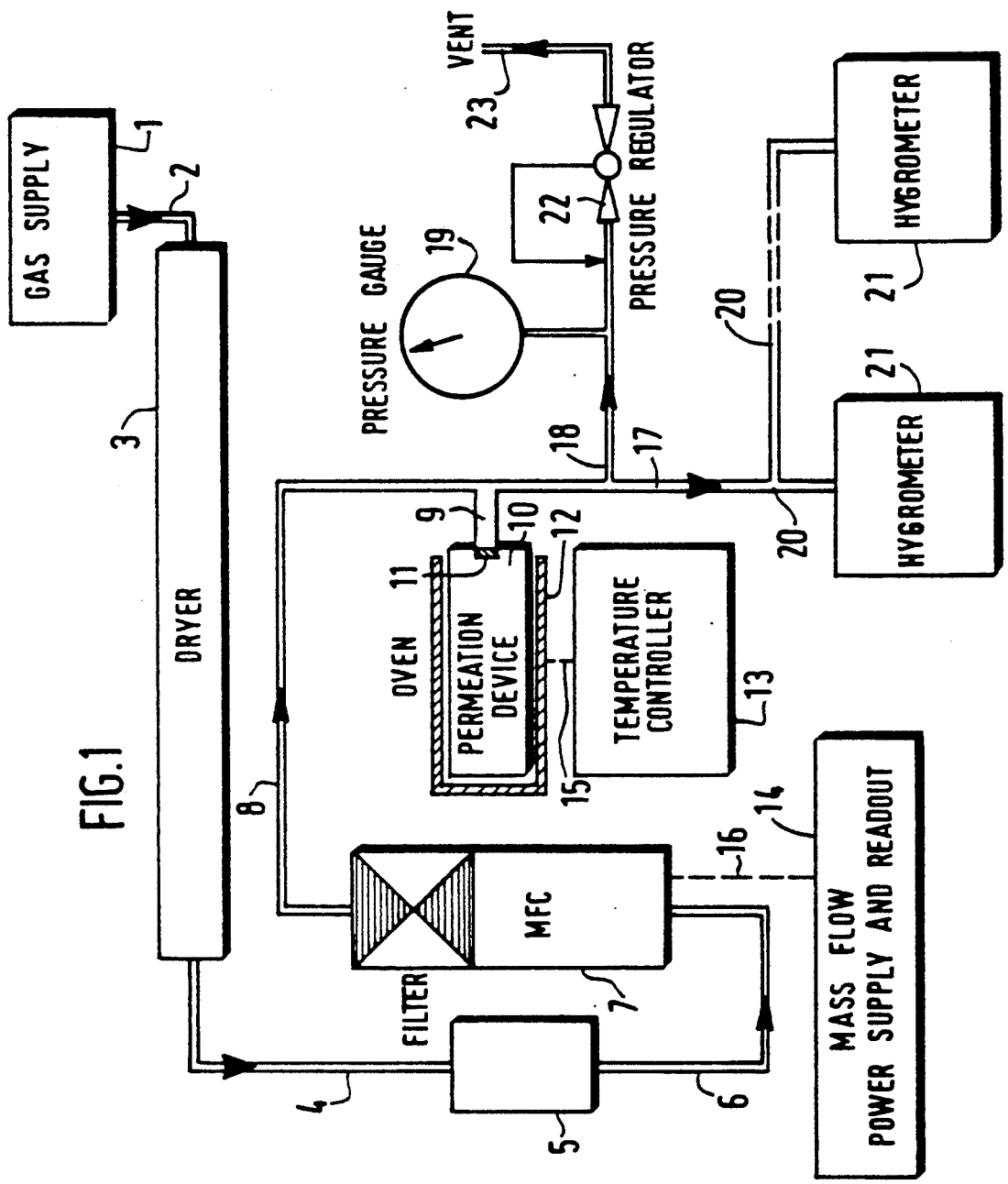
FIG. 1 is a schematic view of gas generating apparatus for calibrating analyzers in accordance with one illustrative embodiment of the invention.

Referring to FIG. 1 of the drawings, a stream of vector or carrier gas from a gas supply 1 is injected via a duct 2 into a scrubber or dryer 3. The dryer 3 is effective to remove water vapor and other undesired gaseous impurities which may exist in the carrier gas, and it illustratively comprises a 9"×¼" i.d. cartridge filled with a conventional drying agent. Alternatively, the dryer may be in the form of a 13X or 5A molecular sieve which is activated at an elevated temperature to remove residual moisture.

The carrier gas leaving the dryer 3 is directed through a duct 4 to a filter 5 which serves to remove particulate material that may be contained in the carrier gas stream. In the illustrated embodiment the filter 5 is a 2um filter which is provided with a discharge duct 6 for the impurity free carrier gas.

The discharge duct 6 is connected to a mass flow controller indicated schematically at 7. The controller 7 illustratively is of the type available commercially under the trademark ALPHAGAZ-841-09, and it discharges a precise constant flow of gas through a duct 8. The controller 7 is provided with a mass flow power supply and readout device 14 and is connected thereto by a line 16. The device 14 supplies power to the controller 7 and provides an external adjustment to vary the flow rate of the impurity free gas being discharged from the controller.

The duct 8 delivers impurity free gas at a precise massic flow rate from the mass flow controller 7 to a T-shaped mixing junction 9. The central portion of the junction 9 is connected to a permeation device 10 having a membrane 11 for discharging a constant flow of water vapor or other impurity gas into the impurity-free stream of carrier gas as it passes the junction 9. The device 10 illustratively is of the type sold under the commercial reference G-CAL Permeation Device by GC Industries, Inc., and according to the above U.S. Pat. No. 4,399,942 the device includes a dimethylpolysiloxane membrane.

The permeation device 10 is maintained at a substantially constant temperature by an oven 12 whose temperature is monitored via a line 15 by a temperature controller 13. The controller 13 may be of the type available commercially from OMEGA Engineering, Inc. under the designation OMEGA CN 300 KC. The oven 12 is in the form of an aluminum enclosure having an inner diameter only slightly greater than the external diameter of the device 10 with a heating element such as a belt wrapped around the enclosure and electrically connected through the line 15 to the temperature controller 13. The oven maintains the outside temperature of the device within a range of 1° C. of the setpoint temperature to hold the moisture concentration within a few percent of the desired concentration, that is, within the range of 0.01 to 10 ppm. H$_2$O.

For a given membrane 11, at a given temperature, the permeation rate P.R. across the membrane would appear to be a linear function of the pressure P of the carrier gas:

$$P.R. = A(D) + B(D) \times P$$

wherein P is the pressure of the carrier gas sweeping the membrane, and A (D) and B (D) are parameters which are dependent on the flow rate D of the carrier gas past the membrane.

The concentration in the vector gas of impurity gas which permeates through the membrane 11 into the T-junction 9 is given by the following formula:

$$C = \frac{K \times PR}{F}$$

wherein

C = concentration of impurity gas in the carrier gas (in p.p.m. - volume)

K = molar gas constant at 25° C. (24.45/molecular weight)

PR = permeation rate of the membrane (10$^{-9}$g/minute) at a given temperature

F = gas flowrate (cc/minute)

The pressure of the carrier gas stream moving past the membrane 11 is controlled by a pressure regulator 22. The regulator 22 illustratively is of the type available commercially from the Nupro Company under the designation Type R 3A series. The regulator 22 is connected by a duct 18 to the duct 8 on the downstream side of the mixing junction 9 and is provided with a suitable pressure gauge 19. If the pressure of the gas in the duct 8 increases above the predetermined pressure set by the regulator 22, the mixture of carrier gas and impurity gas is vented through a vent 23 until the pressure drops to the predetermined pressure. The pressure of the mixture is thus accurately maintained and closely approximates the predetermined pressure in the vicinity of the membrane 11.

The mixing junction 9 is connected by a duct 17 and ducts 20 to one or more hygrometers 21 or other analyzing equipment to be calibrated. The pressure regulator 22 is adjustable to change its pressure threshhold and thereby modify the pressure of the mixture in the ducts 8, 17 and 20 and in the junction 9.

The apparatus of FIG. 1 exhibits particularly good results for the calibration of many types of analyzers in the low ppb range. When the injected impurity is in the gas phase, however, the lifetime of the permeation device is substantially reduced, and its permeation rate is not absolutely constant during this lifetime but instead follows an exponential decay. These difficulties are alleviated, to some extent, by using the apparatus on the asymptotic portion of the curve. For certain calibration mixtures and techniques, it nevertheless remains difficult to maintain a constant permeation across the membrane over an extended period of time.

Figure 2:
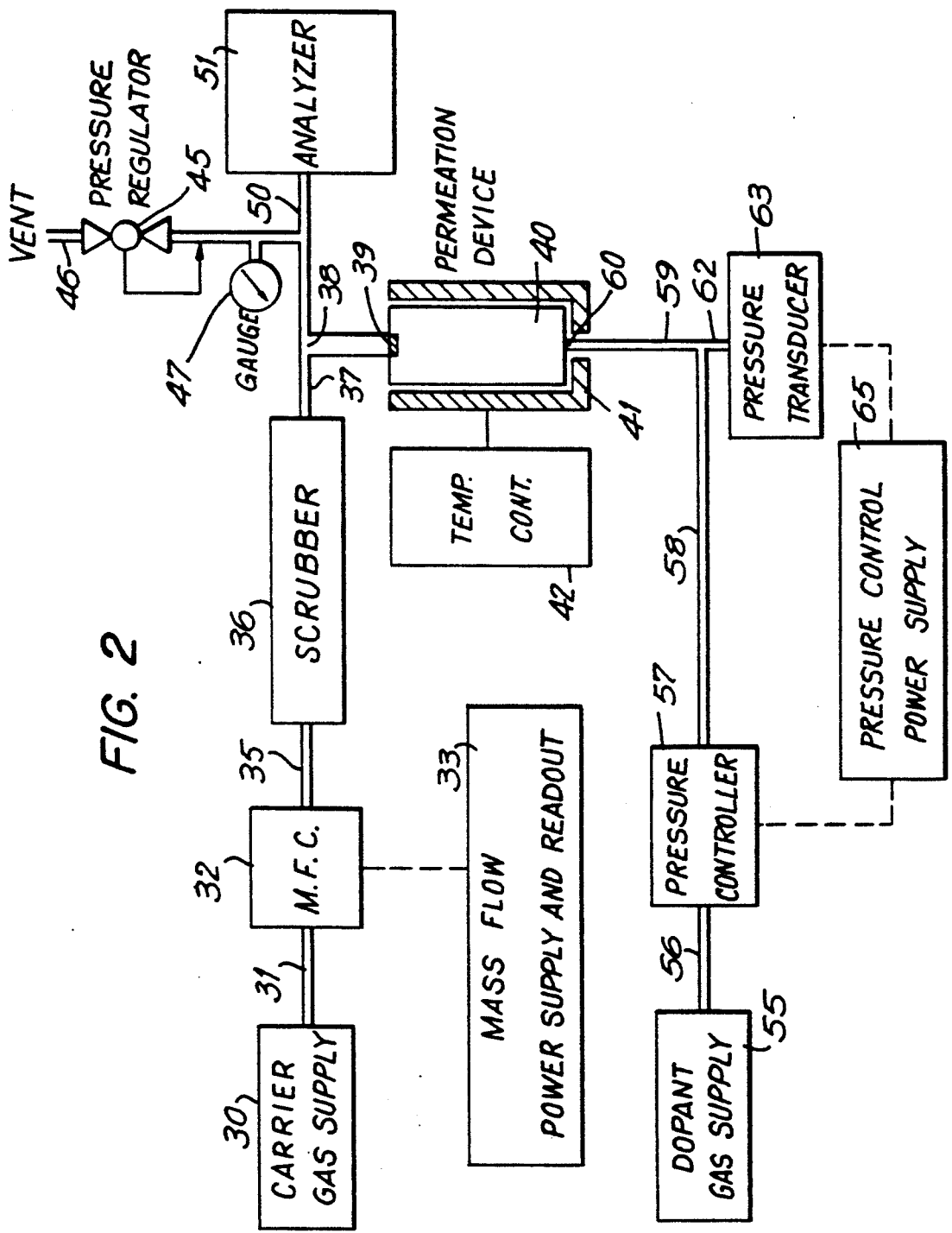
FIG. 2 is a schematic view of gas generating apparatus for calibrating analyzers in accordance with another illustrative embodiment of the invention, for use with gaseous impurities. As used herein, the term "gaseous impurities" refers to impurities in the gas phase under standard conditions of pressure and temperature.

The foregoing disadvantages are substantially reduced by continuously supplying the impurity or dopant gas to the permeation device at a constant pressure. Referring to FIG. 2, for example, there is shown a vector or carrier gas supply 30 which is connected by a duct 31 to a mass flow controller 32. The controller 32 is similar to the controller 7 of FIG. 1 and is provided with a mass flow power supply and readout device 33. The controller 32 discharges the carrier gas at a precise massic flow rate through a duct 35 to a scrubber 36 to remove the carrier gas at least the type of impurity generated by the permeation device. The impurity-free carrier gas from the scrubber 36 proceeds through a duct 37 to a mixing junction 38 of T-shaped configuration.

In a manner similar to that described heretofore, the impurity- free carrier gas within the duct 37 sweeps across the membrane 39 of a permeation device 40. The temperature of the device 40 is controlled by an oven 41 and a temperature controller 42, and the pressure of the gas mixture is kept constant by a pressure regulator 45 and a vent 46 and is monitored by a gauge 47. The mixture is supplied through a duct 50 to one or more analyzers 51.

The apparatus of FIG. 2 is provided with a dopant gas supply 55. Gas from the supply 55 passes through a duct 56 to a pressure controller 57 and then through ducts 58 and 59 to an inlet port 60 at the end of the permeation device 40 opposite that including the membrane 39. The junction of the ducts 58 and 59 is connected by a duct 62 to a pressure transducer 63. The transducer 63 and the pressure controller 57 are provided with a pressure control power supply 65.

Impurity gas from the dopant gas supply 55 is continuously introduced into the permeation device 40 during the lifetime of the membrane 39 and is maintained at a precise constant pressure by the pressure controller 57. The pressure within the device 40 similarly remains constant, and hence there is a constant permeation rate through the membrane. With this arrangement the impurity level in the gas reaching the analyzer 51 is a function only of the flow rate of the impurity-free carrier gas sweeping the membrane as determined by the mass flow controller 32. The pressure of the gas reaching the analyzer may be readily adjusted through the use of the pressure regulator 45.

The terms and expressions which have been employed are used as terms of description and not of limitation, and there is no intention in the use of such terms and expressions of excluding equivalents of the features shown and described, or portions thereof, it being recognized that various modifications are possible within the scope of the invention claimed.

We claim:

1. Gas generating apparatus comprising, in combination:
   a supply of carrier gas containing gaseous impurities;
   metering means connected to said supply of carrier gas and supplied with said carrier gas for discharging said carrier gas at a precise flow rate;
   means for receiving said carrier gas and removing impurities therefrom to provide an impurity-free carrier gas stream;
   a source of a non-liquid substantially only gaseous phase dopant gas;
   impurity generating means for producing a constant flow of impurity gas from said dopant gas, said impurity generating means having a first end coupled to said source of dopant gas to receive the gaseous phase dopant gas therefrom and a second end including a membrane through which the impurity gas permeates;
   a gas conduit interconnecting the source of dopant gas and said first end of said impurity generating means and including gas pressure control means through which dopant gas is supplied from said source to said first end of said impurity generating means and means for monitoring the pressure of the dopant gas supplied to said impurity generating means to control the pressure thereof such that said dopant gas is supplied at a substantially constant pressure thereby maintaining a substantially constant flow rate of said impurity gas through said membrane; and
   means coupled to said second end and to said means for removing impurities from said carrier gas for mixing said impurity gas from said impurity generating means and said impurity-free carrier gas stream, to deliver a gaseous mixture containing a precise amount of said impurity gas in said carrier gas.

2. Gas generating apparatus as defined by claim 1, further comprising a gas analyzer into which said mixture is supplied and analyzed.

3. Gas generating apparatus as defined by claim 1, wherein the metering means comprises a mass flow controller connected to the carrier gas supply.

4. Gas generating apparatus comprising, in combination:
   a supply of carrier gas containing gaseous impurities;
   metering means connected to said supply of carrier gas and supplied with said carrier gas for discharging said carrier gas at a precise flow rate;
   scrubber means for receiving said carrier gas and removing gaseous impurities therefrom to provide an impurity-free carrier gas stream;
   a supply of non-liquid dopant gas;
   impurity generating means for producing a constant flow of impurity gas from said dopant gas, said impurity generating means having a first end coupled to said supply of dopant gas to receive dopant gas therefrom and a second end including a membrane through which the impurity gas permeates;
   pressure monitoring and control means interconnecting the dopant gas supply and the first end of said impurity generating means for monitoring the pressure of the dopant gas supplied to said first end and for controlling same to continuously supply dopant gas to said impurity generating means at a substantially constant pressure such that said impurity gas permeates through said membrane at a substantially constant flow rate;
   means coupled to the second end of said impurity generating means and to said scrubber means for mixing impurity gas permeating through said membrane and said impurity-free carrier gas stream, to deliver a gaseous mixture containing a precise amount of said impurity gas in said carrier gas; and
   pressure regulator means connected to the mixing means for maintaining said gaseous mixture at a generally constant pressure.

5. Gas generating apparatus as defined by claim 4, further comprising a gas analyzer coupled to said means for mixing and supplied with said mixture.

6. Gas generating apparatus as defined by claim 4, wherein the metering means is connected between the carrier gas supply and the scrubber means.

7. Gas generating apparatus as defined by claim 4, wherein the pressure regulator means includes a vent for venting the mixture when its pressure exceeds said generally constant pressure.

8. Gas generating apparatus as defined by claim 4, wherein the dopant gas is supplied to the impurity generating means at a substantially constant but adjustable pressure.

9. Gas generating apparatus as defined by claim 4 wherein the pressure monitoring means includes pressure transducer means for measuring the dopant gas pressure supplied to the impurity generating means.

* * * * *